United States Patent
Sun et al.

(10) Patent No.: US 11,448,592 B2
(45) Date of Patent: Sep. 20, 2022

(54) METHOD FOR RAPIDLY PREDICTING FREEZER STORAGE TIME OF FROZEN PORK BASED ON REFLECTANCE RATIO OF TWO NEAR-INFRARED BANDS

(71) Applicant: SOUTH CHINA UNIVERSITY OF TECHNOLOGY, Guangzhou (CN)

(72) Inventors: Dawen Sun, Guangzhou (CN); Weiwei Cheng, Guangzhou (CN); Hongbin Pu, Guangzhou (CN); Zhiwei Zhu, Guangzhou (CN); Zhong Han, Guangzhou (CN)

(73) Assignee: SOUTH CHINA UNIVERSITY OF TECHNOLOGY, Guangzhou (CN)

(*) Notice: Subject to any disclaimer, the term of this patent is extended or adjusted under 35 U.S.C. 154(b) by 907 days.

(21) Appl. No.: 16/321,042

(22) PCT Filed: Sep. 20, 2017

(86) PCT No.: PCT/CN2017/102451
§ 371 (c)(1),
(2) Date: Jan. 28, 2019

(87) PCT Pub. No.: WO2018/019312
PCT Pub. Date: Feb. 1, 2018

(65) Prior Publication Data
US 2019/0178792 A1 Jun. 13, 2019

(30) Foreign Application Priority Data
Jul. 28, 2016 (CN) .......................... 201610609046.2

(51) Int. Cl.
*G01N 21/359* (2014.01)
*G01N 33/12* (2006.01)
(Continued)

(52) U.S. Cl.
CPC ....... *G01N 21/359* (2013.01); *G01N 21/3563* (2013.01); *G01N 21/59* (2013.01); *G01N 33/12* (2013.01)

(58) Field of Classification Search
CPC .. G01N 21/359; G01N 21/3563; G01N 21/59; G01N 33/12
See application file for complete search history.

(56) References Cited

FOREIGN PATENT DOCUMENTS

| CN | 103424374 A | 12/2013 |
|---|---|---|
| CN | 104568796 A | 4/2015 |

(Continued)

OTHER PUBLICATIONS

Prado et al., On-Site NIR Spectroscopy to Control the Shelf Life of Pork Meat, Feb. 19, 2011, Food Anal. Methods. vol. 4, pp. 582-589. (Year: 2011).*

(Continued)

*Primary Examiner* — Christine S. Kim
(74) *Attorney, Agent, or Firm* — JMB Davis Ben-David

(57) ABSTRACT

The invention discloses a method for rapidly predicting freezer storage time of frozen pork based on reflectance ratio of two near-infrared bands. Firstly, the near-infrared spectra information of the frozen pork is obtained by a near-infrared spectrometer, and the near-infrared spectra are analyzed to obtain center values of bands centered on 1500 nm, 1350 nm and 1890 nm characteristic peaks. The ratio thereof is treated as a eigenvector, which is substituted into the characteristic exponential function based on the eigenvector and freezer storage time to calculate the freezer storage time of frozen pork. By near-infrared spectroscopy technology, the invention directly detects the freezer storage time of pork in a frozen state, significantly reduces the time required by the conventional method, and has the advantages of being fast and non-destructive.

6 Claims, 3 Drawing Sheets

(51) Int. Cl.
      *G01N 21/59*      (2006.01)
      *G01N 21/3563*   (2014.01)

(56) References Cited

FOREIGN PATENT DOCUMENTS

| | | |
|---|---|---|
| CN | 105136709 A | 9/2015 |
| CN | 106153576 A | 11/2016 |
| JP | 2002328088 A | 11/2002 |

OTHER PUBLICATIONS

Prevolnik et al., Ability of NIR spectroscopy to predict meat chemical composition and quality—a review, 2004, Czech J. Anim. Sci., vol. 49, pp. 500-510. (Year: 2004).*

Wu et al., Mapping of TBARS distribution in frozen-thawed pork using NIR hyperspectral imaging, Nov. 10, 2015, Meat Science, vol. 113, p. 92-96. (Year: 2015).*

Park et al., Evaluation of Pork Loin Freshness Using Absorbance Characteristic of Near-Infrared, Feb. 2, 2008, Biological Engineering vol. 1, pp. 173-180. (Year: 2008).*

Cai, Jianrong, et al. "Detection of rust in citrus by hyperspectral imaging technology and band ratio algorithm." Transactions of the Chinese Society of Agricultural Engineering 25.1 (2009): 127-131.

* cited by examiner

METHOD FOR RAPIDLY PREDICTING FREEZER STORAGE TIME OF FROZEN PORK BASED ON REFLECTANCE RATIO OF TWO NEAR-INFRARED BANDS

CROSS-REFERENCE TO RELATED APPLICATIONS

This is the U.S. National Stage of International Application No. PCT/CN2017/102451 filed Sep. 20, 2017, which was published in Chinese under PCT Article 21(2), and which in turn claims the benefit of China Patent Application No. 201610609046.2, filed Jul. 28, 2016.

FIELD

The invention relates to a detection method for the freezer storage time of frozen pork, in particular to a method for rapidly predicting freezer storage time of frozen pork based on reflectance ratio of two near-infrared bands.

BACKGROUND ART

Pork is one of the most consumed meats in China, but fresh pork is highly prone to spoilage due to its rich protein, fin and other nutrients. In order to extend the shelf life of pork, in the past few decades, although there have been many preservation methods emerged, preservation in freezer is still one of the most important ways of preserving meat, and frozen meat is the main form of meat circulating in the market. Under frozen condition, although the shelf life of fresh meat is greatly extended, with the increase of freezer storage time and factors like temperature fluctuations and repeated freezing and thawing, the protein and fat will gradually decompose to produce corrosive and irritating substances including methylamine, cadaverine, methane and methyl hydrazine, etc., which cause deterioration of meat quality. The deterioration degree of meat quality is usually proportional to the freezer storage time. Therefore, it is important to test the freezer storage time of frozen pork to evaluate the quality of frozen pork and ensure food safety. In particular, in last year media reports on the "zombie meat" caused great concern about the freezer storage time of frozen meat. The freezing technology has played a positive role in the preservation of meat, but freezing also affects the quality of the meat, making the identification of the freezer storage time of frozen meat more difficult than fresh meat. In the detection of frozen meat quality, most of the traditional methods are to first unfreeze the frozen meat, and then determine its quality, which damages the samples, includes complicated steps and is time consuming. The use of rapid and non-destructive testing technology to detect the freezer storage time of frozen meat is of great significance for the safety of meat. However, there are few reports on rapid and non-destructive test of frozen meat.

The near-infrared spectroscopy records mainly the overtone and combination tone of the vibration of the organic hydrogen-containing group XH (X=C, N, O). The near-infrared absorption wavelength and intensity of different groups (such as methyl, methylene, benzene ring, etc.) or the same group in different chemical environments are significantly different, therefore near-infrared spectrum contains rich information of structure and composition, which makes it suitable for the measurement of the composition and properties of hydrocarbon organic materials. At present, there are some reports on the detection of meat quality using near-infrared spectroscopy. These reports are mostly concentrated on the detection of meat quality at room temperature. For example, the Chinese invention patent CN102590103A discloses a near-infrared meat detector and detection method; Chinese invention patent CN104568796A discloses a detection method of freezer storage time of pork based on visible/near infrared spectroscopy; Chinese invention patent CN102519906B discloses a simultaneous multi-parameter detection method of beef quality by multi-channel near-infrared spectrum. As for the detection of frozen meat quality, Chinese invention patent CN105136709A discloses a method for measuring the freezing parameters of frozen meat in and device thereof, which detects the freezing temperature and the freezing rate of the frozen product rapidly through a model based on stoichiometric relationship between the frozen parameter and the near-infrared spectrum. However, there is still a lack of a rapid and simple detection method for the freezer storage time of frozen pork.

SUMMARY OF THE INVENTION

In order to overcome the above disadvantages and disadvantages of the prior art, the present invention provides a method for rapidly predicting freezer storage time of frozen pork based on reflectance ratio of two near-infrared bands, which directly detects the freezer storage time of pork in a frozen state and has the advantages of being fast and non-destructive.

The object of the invention is achieved by the following technical solutions:

A method for rapidly predicting freezer storage time of frozen pork based on reflectance ratio of two near-infrared bands comprises the steps of:

(1) scanning frozen pork and calibrating to obtain near-infrared spectrum of the frozen pork;

(2) calculating a center value $R_{m1350}$ of a band centered on a 1350 nm characteristic peak, a center value $R_{m1980}$ of a band centered on a 1890 nm characteristic peak and a center value $R_{m1500}$ of a band centered on a 1500 nm reference peak in the near-infrared spectrum of the frozen pork:

$$R_{m1350}=R_{1348}\times0.1+R_{1349}\times0.2+R_{1350}\times0.4+R_{1351}\times0.2+R_{1352}\times0.1$$

$$R_{m1890}=R_{1888}\times0.1+R_{1889}\times0.2+R_{1890}\times0.4+R_{1891}\times0.2+R_{1892}\times0.1$$

$$R_{m1500}=R_{1498}\times0.1+R_{1499}\times0.2+R_{1500}\times0.4+R_{1551}\times0.2+R_{1552}\times0.1$$

wherein $R_{1348}$, $R_{1349}$, $R_{1350}$, $R_{1351}$, $R_{1352}$, $R_{1888}$, $R_{1889}$, $R_{1890}$, $R_{1891}$, $R_{1892}$, $R_{1498}$, $R_{1499}$, $R_{1500}$, $R_{1551}$, $R_{1552}$ are reflectance of the frozen pork at 1348 nm, 1349 nm, 1350 nm, 1351 nm, 1352 nm, 1888 nm, 1889 nm, 1890 nm, 1891 nm, 1892 nm, 1498 nm, 1499 nm, 1500 nm, 1501 nm, 1502 nm, respectively;

(3) calculating a standard center value $S_{m1890}$ of the characteristic band centered on 1890 nm:

$$S_{m1890}=R_{m1890}/R_{m1500}$$

(4) treating the ratio of $R_{m1350}$ to $S_{m1890}$ as an eigenvector I, i.e., $I=R_{m1350}/S_{m1890}$;

(5) substituting the eigenvector I into a characteristic exponential function $t=1E+07e^{-97.34I}$ which is based on the eigenvector I and freezer storage time t, so as to predict the freezer storage time of the frozen pork.

The characteristic exponential function based on the eigenvector I and freezer storage time in step (5) is obtained by the following steps:

(a) picking frozen pork training samples from pork with different freezer storage time, scanning the frozen pork training samples and calibrating to obtain near-infrared spectra of the frozen pork;

(b) calculating a center value $R'_{m1350}$ of a band centered on a 1350 nm characteristic peak, a center value $R'_{m1980}$ of a band centered on a 1890 nm characteristic peak and a center value $R'_{m1500}$ of a band centered on a 1500 nm reference peak in the near-infrared spectrum of each of the frozen pork training samples:

$$R'_{m1350}=R'_{1348}\times0.1+R'_{1349}\times0.2+1350\times0.4+R'_{1351}\times0.2+R'_{1352}\times0.1$$

$$R'_{m1890}=R'_{1888}\times0.1+R'_{1889}\times0.2+1890\times0.4+R'_{1891}\times0.2+R'_{1892}\times0.1$$

$$R'_{m1500}=R'_{1498}\times0.1+R'_{1499}\times0.2+R'_{1500}\times0.4+R'_{1551}\times0.2+R'_{1552}\times0.1$$

wherein $R'_{1348}$, $R'_{1349}$, $R'_{1350}$, $R'_{1351}$, $R'_{1352}$, $R'_{1888}$, $R'_{1889}$, $R'_{1890}$, $R'_{1891}$, $R'_{1892}$, $R'_{1498}$, $R'_{1499}$, $R'_{1500}$, $R'_{1551}$, $R'_{1552}$ are reflectance of the frozen pork training samples at 1348 nm, 1349 nm, 1350 nm, 1351 nm, 1352 nm, 1888 nm, 1889 nm, 1890 nm, 1891 nm, 1892 nm, 1498 nm, 1499 nm, 1500 nm, 1501 nm, 1502 nm, respectively;

(c) calculating a standard center value $S_{m1890}$ of the characteristic band centered on 1890 nm of the frozen pork training samples:

$$S'_{m1890}=R'_{m1890}/R'_{m1500}$$

(d) treating the ratio of $R'_{m1350}$ to $S'_{m1890}$ as an training eigenvector I' of the frozen pork training samples, i.e., $I'=R'_{m1350}/S'_{m1890}$;

(e) establishing a model based on the training eigenvector the frozen pork training samples to obtain a characteristic exponential function $t=1E+07e^{-97.34I}$ which is based on the eigenvector I and freezer storage time t.

The different freezer storage time of the pork are 1, 3, 6, 9, and 12 months, respectively.

The regression coefficient of the characteristic exponential function based on the eigenvector I and the freezer storage time t is 0.9953.

The prediction coefficient of determination of the characteristic exponential function based on the eigenvector I and the freezer storage time t is 0.9947, and the prediction root mean square error is 0.1256 month.

Said scanning the frozen pork training samples in step (a) is specifically scanning the frozen pork training samples in a frozen state;

and said scanning the frozen pork in step (1) is specifically scanning the frozen pork in a frozen state.

The principle of the invention is as follows:

In the near-infrared spectrum of frozen pork, with the increase of freezer storage time, the ratio of the reflectance of OH combination tone of water molecules near 1890 nm to that of OH first-order overtone of water molecules near 1500 nm remains basically the same, and the reflectance of the CH combination tone of protein and fat near 1350 nm significantly decreases. The present invention utilizes the ratio between near-infrared characteristic bands to rapidly predict the freezer storage time of frozen pork. method.

Compared with the prior art, the present invention has the following advantages:

(1) In the present invention, the frozen storage time of pork is directly detected in a frozen state, which has the advantage of being fast and non-destructive. It overcomes the defects in the prior art that the frozen meat should be firstly unfrozen and then freshness index thereof are measured, which damages the samples, has complicated steps and is time-consuming.

(2) The method for rapidly predicting freezer storage time of frozen pork based on reflectance ratio of two near-infrared bands of the present invention involves a characteristic exponential function based on the eigenvector I and the freezer storage time, the regression coefficient of which can reach 0.995, the prediction coefficient of determination of which can reach 0.9947, and the prediction root mean square error of which is only 0.1256 month, therefore the test results are accurate.

DETAILED DESCRIPTION OF THE EMBODIMENTS

The present invention will be further described in detail below with reference to the embodiments, but the embodiments of the present invention are not limited thereto.

Example 1

The training process of a method for rapidly predicting freezer storage time of frozen pork based on reflectance ratio of two near-infrared bands is as follows:

(1) Fresh pork samples were selected and cut into a size of 4 cm×5 cm×10 cm, and 100 pieces of samples with a weight of about 200 g were obtained. 20 pieces were used as a group so that there were a total of 5 sets, all of which were frozen at −40° C. and stored.

Figure 1:
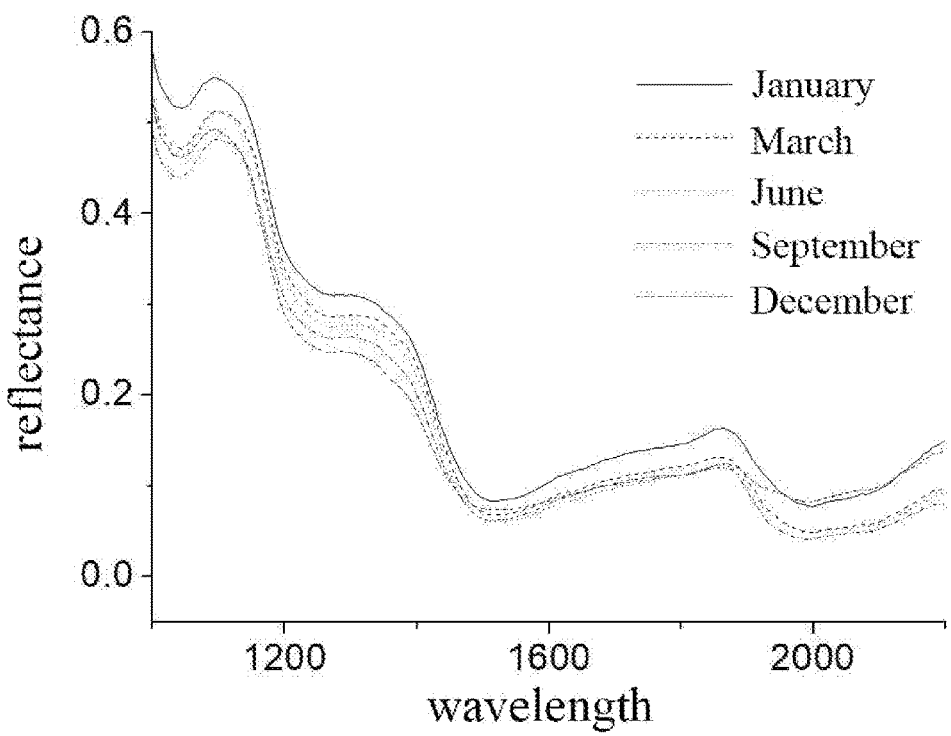
FIG. 1 shows near-infrared spectra of frozen pork training samples with different freezer storage times according to an embodiment of the present invention.

(2) One group of frozen pork was taken out after 1, 3, 6, 9, and 12 months respectively, and the frozen pork samples were scanned and calibrated by near-infrared spectroscopy to obtain near-infrared spectra of 100 frozen pork samples. Assign 60 to the training set and 40 to the verification set. The near-infrared spectra of the frozen pork training samples obtained in this example with different freezer storage times is shown in FIG. 1.

(3) The near-infrared spectra of the frozen pork training samples was analyzed. The ratio among the center value of the band centered on 1350 nm characteristic peak, the center value of the band centered on 1500 nm characteristic peak and the center value of the band centered on 1890 nm characteristic peak were used as training eigenvector to calculate the characteristic exponential function based on the eigenvector I and the freezer storage time t.

(3-1) The following weight functions were used to calculate a center value $R'_{m1350}$ of a band centered on a 1350 nm characteristic peak, a center value $R'_{m1980}$ of a band centered on a 1890 nm characteristic peak and a center value $R'_{m1500}$ of a band centered on a 1500 nm reference peak in the near-infrared spectrum of each of the frozen pork training samples:

$$R'_{m1350}=R'_{1348}\times0.1+R'_{1349}\times0.2+R'_{1350}\times0.4+R'_{1351}\times0.2+R'_{1352}\times0.1$$

$$R'_{m1890}=R'_{1888}\times0.1+R'_{1889}\times0.2+R'_{1890}\times0.4+R'_{1891}\times0.2+R'_{1892}\times0.1$$

$$R'_{m1500}=R'_{1498}\times0.1+R'_{1499}\times0.2+R'_{1500}\times0.4+R'_{1551}\times0.2+R'_{1552}\times0.1$$

wherein $R'_{1348}$, $R'_{1349}$, $R'_{1350}$, $R'_{1351}$, $R'_{1352}$, $R'_{1888}$, $R'_{1889}$, $R'_{1890}$, $R'_{1891}$, $R'_{1892}$, $R'_{1498}$, $R'_{1499}$, $R'_{1500}$, $R'_{1551}$, $R'_{1552}$ are reflectance of the frozen pork training samples at 1348 nm, 1349 nm, 1350 nm, 1351 nm, 1352 nm, 1888 nm, 1889 nm, 1890 nm, 1891 nm, 1892 nm, 1498 nm, 1499 nm, 1500 nm, 1501 nm, 1502 nm, respectively;

(3-2) A standard center value $S_{m1890}$ of the characteristic band centered on 1890 nm of the frozen pork training samples was calculated:

$$S'_{m1890}=R'_{m1890}/R'_{m1500}$$

Figure 2:
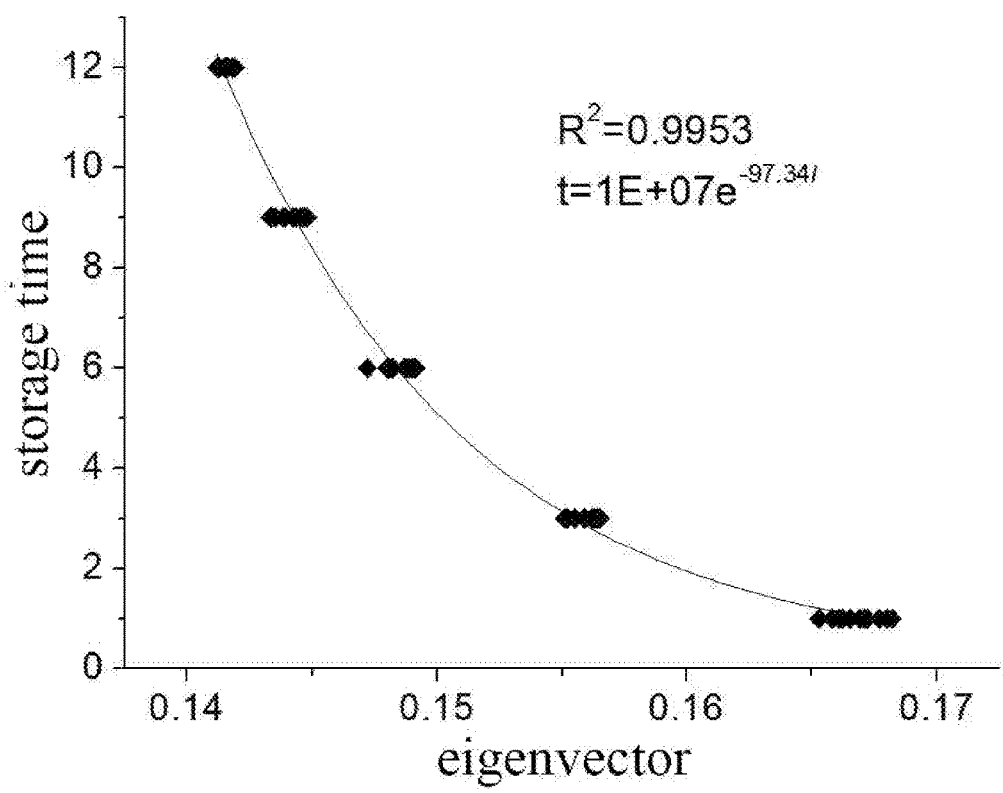
FIG. 2 is the characteristic exponential function of an embodiment of the present invention.

(3-3) The ratio of $R'_{m1350}$ to $S'_{m1890}$ was treated as an training eigenvector of the frozen pork training samples, i.e., $I'=R'_{m1350}/S'_{m1890}$;

(3-4) A model was established based on the training eigenvector the frozen pork training samples to obtain a characteristic exponential function $t=1E+07e^{-97.34I}$ which is based on the eigenvector I and freezer storage time t and is shown in FIG. 2.

Figure 3:
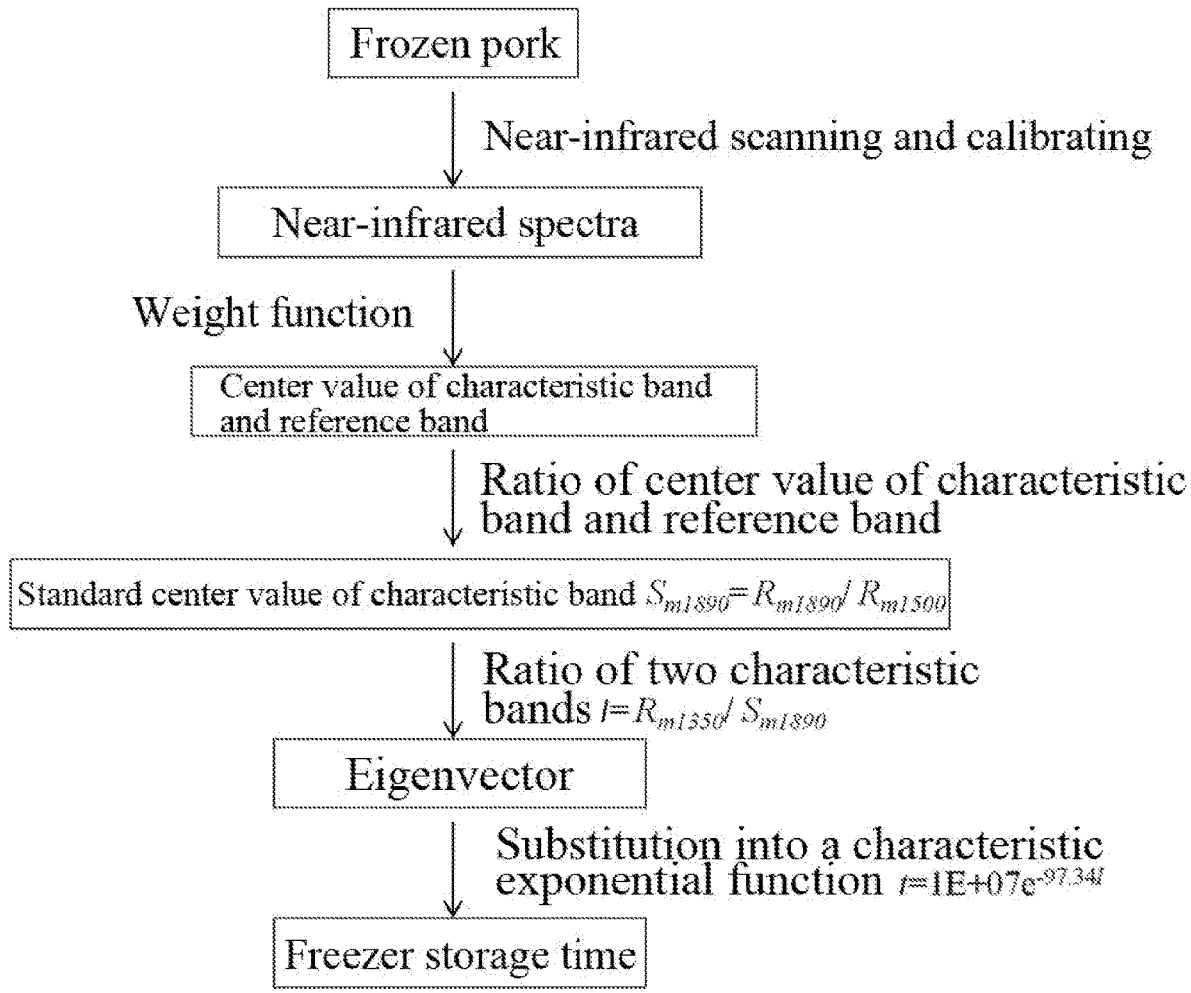
FIG. 3 is a testing procedure of the method for rapidly predicting freezer storage time of frozen pork based on reflectance ratio of two near-infrared bands according to the embodiment of the present invention.

As shown in FIG. 3, a testing procedure of the method for rapidly predicting freezer storage time of frozen pork based on reflectance ratio of two near-infrared bands of the example is as follows:

(1) Frozen pork was scanned and calibrated to obtain near-infrared spectrum of the frozen pork;

(2) A center value $R_{m1350}$ of a band centered on a 1350 nm characteristic peak in the near-infrared spectrum of the frozen pork, a center value $R_{m1980}$ of a band centered on a 1890 nm characteristic peak and a center value $R_{m1500}$ of a band centered on a 1500 nm reference peak were calculated respectively:

$$R_{m1350}=R_{1348}\times0.1+R_{1349}\times0.2+R_{1350}\times0.4+R_{1351}\times0.2+R_{1352}\times0.1$$

$$R_{m1890}=R_{1888}\times0.1+R_{1889}\times0.2+R_{1890}\times0.4+R_{1891}\times0.2+R_{1892}\times0.1$$

$$R_{m1500}=R_{1498}\times0.1+R_{1499}\times0.2+R_{1500}\times0.4+R_{1551}\times0.2+R_{1552}\times0.1$$

wherein $R_{1348}$, $R_{1349}$, $R_{1350}$, $R_{1351}$, $R_{1352}$, $R_{1888}$, $R_{1889}$, $R_{1890}$, $R_{1891}$, $R_{1892}$, $R_{1498}$, $R_{1499}$, $R_{1500}$, $R_{1551}$, $R_{1552}$ are reflectance of the frozen pork at 1348 nm, 1349 nm, 1350 nm, 1351 nm, 1352 nm, 1888 nm, 1889 nm, 1890 nm, 1891 nm, 1892 nm, 1498 nm, 1499 nm, 1500 nm, 1501 nm, 1502 nm, respectively;

(3) A standard center value $S_{m1890}$ of the characteristic band centered on 1890 nm was calculated:

$$S_{m1890}=R_{m1890}/R_{m1500}$$

Figure 4:
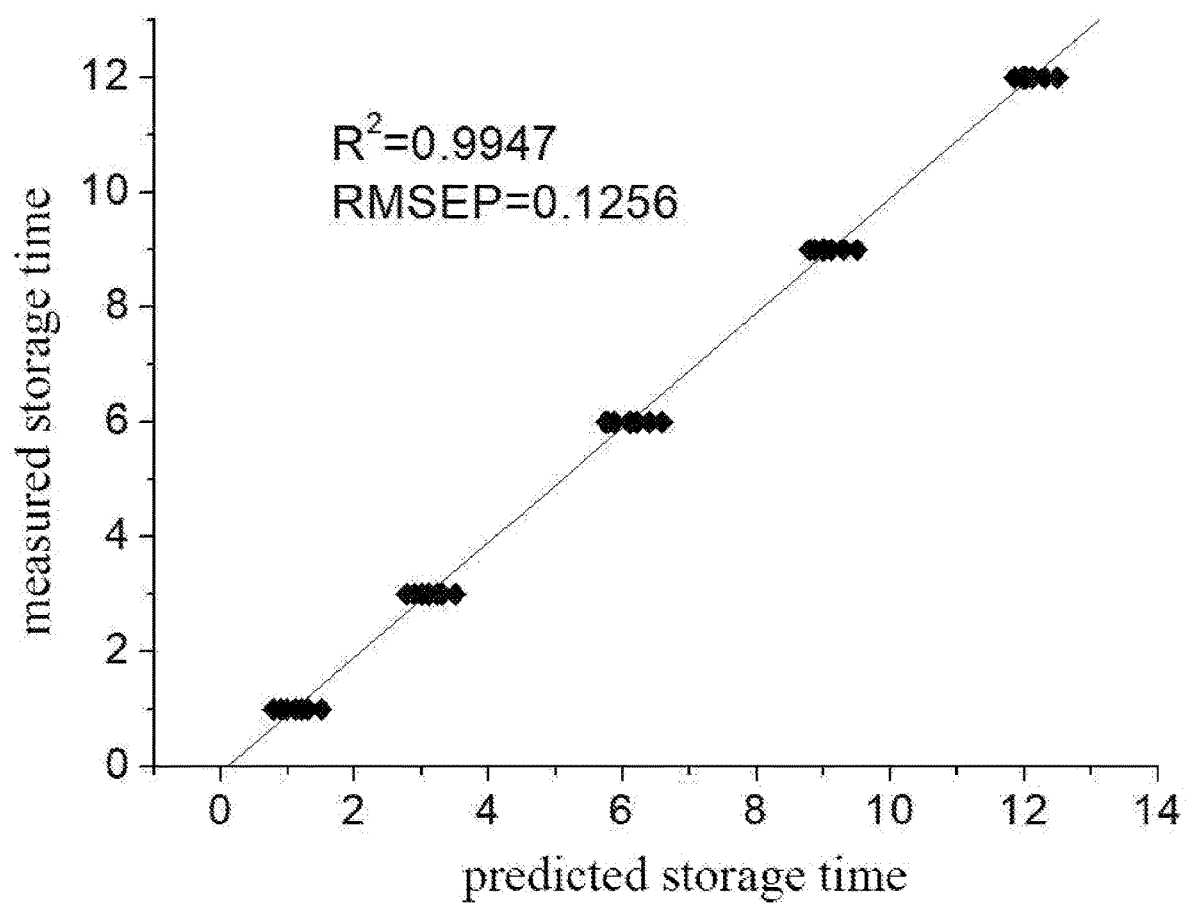
FIG. 4 is a graph comparing calculated freezer storage times and actual freezer storage times of prediction set samples according to an embodiment of the present invention.

(4) The ratio of $R_{m1350}$ to $S_{m1890}$ was treated as an eigenvector I, i.e., $R_{m1350}/S_{m1890}$;

(5) The eigenvector I was substituted into a characteristic exponential function $t=1E+07e^{-97.34I}$ which is based on the eigenvector I and freezer storage time t, so as to predict the freezer storage time of the frozen pork. As shown in FIG. 4, the prediction coefficient of determination is 0.9947, and the prediction root mean square error is only 0.1256 months.

The above embodiments are preferred embodiments of the present invention, but the embodiments of the present invention are not limited to the embodiments, and any other changes, modifications, substitutions, combinations and simplification made without departing from the spirit and scope of the present invention are equivalent replacement means, and are included in the scope of protection of the present invention.

We claim:

1. A method for rapidly predicting freezer storage time of frozen pork based on reflectance ratio of two near-infrared bands, characterized in that, it comprises the steps of:
   (1) scanning frozen pork and calibrating to obtain near-infrared spectrum of the frozen pork;
   (2) calculating a center value $R_{m1350}$ of a band centered on a 1350 nm characteristic peak, a center value $R_{m1980}$ of a band centered on a 1890 nm characteristic peak and a center value $R_{m1500}$ of a band centered on a 1500 nm reference peak in the near-infrared spectrum of the frozen pork:

$$R_{m1350}=R_{1348}\times0.1+R_{1349}\times0.2+R_{1350}\times0.4+R_{1351}\times0.2+R_{1352}\times0.1$$

$$R_{m1890}=R_{1888}\times0.1+R_{1889}\times0.2+R_{1890}\times0.4+R_{1891}\times0.2+R_{1892}\times0.1$$

$$R_{m1500}=R_{1498}\times0.1+R_{1499}\times0.2+R_{1500}\times0.4+R_{1551}\times0.2+R_{1552}\times0.1$$

wherein $R_{1348}$, $R_{1349}$, $R_{1350}$, $R_{1351}$, $R_{1352}$, $R_{1888}$, $R_{1889}$, $R_{1890}$, $R_{1891}$, $R_{1892}$, $R_{1498}$, $R_{1499}$, $R_{1500}$, $R_{1551}$, $R_{1552}$ are reflectance of the frozen pork at 1348 nm, 1349 nm, 1350 nm, 1351 nm, 1352 nm, 1888 nm, 1889 nm, 1890 nm, 1891 nm, 1892 nm, 1498 nm, 1499 nm, 1500 nm, 1501 nm, 1502 nm, respectively;

(3) calculating a standard center value $S_{m1890}$ of the characteristic band centered on 1890 nm:

$$S_{m1890}=R_{m1890}/R_{m1500}$$

(4) treating the ratio of $R_{m1350}$ to $S_{m1890}$ as an eigenvector I, wherein $I=R_{m1350}/S_{m1890}$;
   (5) substituting the eigenvector I into a characteristic exponential function $t=1E+07e^{-97.34I}$ which is based on the eigenvector I and freezer storage time t, so as to predict the freezer storage time of the frozen pork.

2. The method for rapidly predicting freezer storage time of frozen pork based on reflectance ratio of two near-infrared bands according to claim 1, characterized in that, the characteristic exponential function based on the eigenvector I and freezer storage time is obtained by the following steps:
   (a) picking frozen pork training samples from pork with different freezer storage time, scanning the frozen pork training samples and calibrating to obtain near-infrared spectra of the frozen pork;
   (b) calculating a center value $R'_{m1350}$ of a band centered on a 1350 nm characteristic peak, a center value $R'_{m1980}$ of a band centered on a 1890 nm characteristic peak and a center value $R'_{m1500}$ of a band centered on a 1500 nm reference peak in the near-infrared spectrum of each of the frozen pork training samples:

$$R'_{m1350}=R'_{1348}\times0.1+R'_{1349}\times0.2+R'_{1350}\times0.4+R'_{1351}\times0.2+R'_{1352}\times0.1$$

$$R'_{m1890}=R'_{1888}\times0.1+R'_{1889}\times0.2+R'_{1890}\times0.4+R'_{1891}\times0.2+R'_{1892}\times0.1$$

$$R'_{m1500}=R'_{1498}\times0.1+R'_{1499}\times0.2+R'_{1500}\times0.4+R'_{1551}\times0.2+R'_{1552}\times0.1$$

wherein $R'_{1348}$, $R'_{1349}$, $R'_{1350}$, $R'_{1351}$, $R'_{1352}$, $R'_{1888}$, $R'_{1889}$, $R'_{1890}$, $R'_{1891}$, $R'_{1892}$, $R'_{1498}$, $R'_{1499}$, $R'_{1500}$, $R'_{1551}$, $R'_{1552}$ are reflectance of the frozen pork training samples at 1348 nm, 1349 nm, 1350 nm, 1351 nm, 1352 nm, 1888 nm, 1889 nm, 1890 nm, 1891 nm, 1892 nm, 1498 nm, 1499 nm, 1500 nm, 1501 nm, 1502 nm, respectively;

(c) calculating a standard center value $S_{m1890}$ of the characteristic band centered on 1890 nm of the frozen pork training samples:

$$S'_{m1890}=R'_{m1890}/R'_{m1500}$$

(d) treating the ratio of $R'_{m1350}$ to $S'_{m1890}$ as an training eigenvector I' of the frozen pork training samples, wherein $I'=R'_{m1350}/S'_{m1890}$;

(e) establishing a model based on the training eigenvector the frozen pork training samples to obtain a characteristic exponential function $t=1E+07e^{-97.34I'}$—which is based on the training eigenvector I' and freezer storage time t.

3. The method for rapidly predicting freezer storage time of frozen pork based on reflectance ratio of two near-infrared bands according to claim 2, wherein the different freezer storage time of the pork are 1, 3, 6, 9, and 12 months, respectively.

4. The method for rapidly predicting freezer storage time of frozen pork based on reflectance ratio of two near-infrared bands according to claim 2, wherein a regression coefficient of the characteristic exponential function based on the eigenvector I and the freezer storage time t is 0.9953.

5. The method for rapidly predicting freezer storage time of frozen pork based on reflectance ratio of two near-infrared bands according to claim 2, wherein a prediction coefficient of determination of the characteristic exponential function based on the eigenvector I and the freezer storage time t is 0.9947, and a prediction root mean square error is 0.1256 month.

6. The method for rapidly predicting freezer storage time of frozen pork based on reflectance ratio of two near-infrared bands according to claim 2, wherein said scanning the frozen pork training samples in step (a) is specifically scanning the frozen pork training samples in a frozen state;

and said scanning the frozen pork in step (1) is specifically scanning the frozen pork in a frozen state.

\* \* \* \* \*